(12) United States Patent
Roberts

(10) Patent No.: US 12,209,694 B2
(45) Date of Patent: Jan. 28, 2025

(54) LEVER FOR AUTO INSERTION AND SECURE PLACEMENT OF IV TUBING FOR USE IN INTRAVENOUS PUMP SYSTEMS

(71) Applicant: CareFusion 303, Inc., San Diego, CA (US)

(72) Inventor: Steve Roberts, Lakeside, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 18/532,990

(22) Filed: Dec. 7, 2023

(65) Prior Publication Data

US 2024/0142022 A1    May 2, 2024

Related U.S. Application Data

(63) Continuation of application No. 16/832,363, filed on Mar. 27, 2020, now Pat. No. 11,892,108, which is a (Continued)

(51) Int. Cl.
*A61M 5/36* (2006.01)
*A61M 5/00* (2006.01)
(Continued)

(52) U.S. Cl.
CPC .................. *F16L 3/10* (2013.01); *A61M 5/00* (2013.01); *A61M 5/142* (2013.01);
(Continued)

(58) Field of Classification Search
CPC ............. A61M 5/14228; A61M 5/365; A61M 39/281; A61M 39/284; F16L 3/10
See application file for complete search history.

(56) References Cited

U.S. PATENT DOCUMENTS 3,217,712 A   11/1965 Blumenstein et al.
5,364,364 A   11/1994 Kasvikis et al.
(Continued)

FOREIGN PATENT DOCUMENTS

CN   101084027 A   12/2007
CN   102770173 A   11/2012
(Continued)

OTHER PUBLICATIONS

Australian Office Action for Application No. 2018354266, dated Aug. 31, 2023, 4 pages.
(Continued)

*Primary Examiner* — Nkeisha Smith
(74) *Attorney, Agent, or Firm* — Morgan, Lewis & Bockius LLP

(57) ABSTRACT

An infusion pump is provided that includes a housing, a door assembly coupled to the housing, a sensor disposed within the housing and a lever disposed within the housing. The lever includes a first end comprising a wall configured to engage an infusion tubing, a second end comprising a pocket, a spring disposed in the pocket, the spring configured to bias the lever against the door assembly and a pusher disposed on the first end, the pusher configured to align the infusion tubing with the sensor when the door assembly is closed. A method of operating the infusion pump is also provided.

20 Claims, 8 Drawing Sheets

Related U.S. Application Data continuation of application No. 15/793,513, filed on Oct. 25, 2017, now Pat. No. 10,639,417.

(51) Int. Cl.
*A61M 5/142* (2006.01)
*A61M 39/28* (2006.01)
*F16L 3/10* (2006.01)

(52) U.S. Cl.
CPC ........ *A61M 5/14228* (2013.01); *A61M 5/365* (2013.01); *A61M 39/281* (2013.01); *A61M 39/284* (2013.01)

(56) References Cited

U.S. PATENT DOCUMENTS

| | | | | |
|---|---|---|---|---|
| 5,462,256 | A * | 10/1995 | Minick | A61M 39/284 |
| | | | | 604/153 |
| 5,630,710 | A * | 5/1997 | Tune | A61M 5/172 |
| | | | | 417/326 |
| 5,658,133 | A * | 8/1997 | Anderson | A61M 5/172 |
| | | | | 73/19.1 |
| 5,658,712 | A | 8/1997 | Steinmann et al. | |
| 5,868,712 | A * | 2/1999 | Briggs | A61M 5/365 |
| | | | | 417/63 |
| 7,611,498 | B2 * | 11/2009 | Hasler | A61M 5/14228 |
| | | | | 604/151 |
| 8,986,252 | B2 * | 3/2015 | Cummings | A61M 5/14232 |
| | | | | 417/477.2 |
| 9,017,297 | B2 * | 4/2015 | Travis | A61M 39/287 |
| | | | | 604/250 |
| 9,060,920 | B2 * | 6/2015 | Hirabuki | A61J 1/2089 |
| 10,603,480 | B2 * | 3/2020 | Sullivan | A61M 39/12 |
| 11,045,599 | B2 * | 6/2021 | Schieve | A61M 5/142 |
| 11,707,615 | B2 * | 7/2023 | Baier | A61M 5/142 |
| | | | | 604/153 |
| 2009/0043252 | A1 | 2/2009 | Haylor et al. | |
| 2012/0191059 | A1 * | 7/2012 | Cummings | A61M 39/281 |
| | | | | 604/257 |
| 2013/0138074 | A1 * | 5/2013 | Travis | A61M 39/287 |
| | | | | 604/151 |
| 2015/0202362 | A1 * | 7/2015 | Wolff | G06F 1/1681 |
| | | | | 604/152 |
| 2017/0165414 | A1 * | 6/2017 | Schieve | A61M 5/142 |
| 2017/0281865 | A1 * | 10/2017 | Wells | A61M 5/14228 |

FOREIGN PATENT DOCUMENTS

| | | |
|---|---|---|
| CN | 104043158 A | 9/2014 |
| CN | 105705180 A | 6/2016 |
| CN | 105848694 A | 8/2016 |
| CN | 106029125 A | 10/2016 |
| CN | 106535965 A | 3/2017 |
| JP | 2015198811 A | 11/2015 |
| WO | WO-9814234 A1 | 4/1998 |
| WO | WO-9856441 | 12/1998 |
| WO | WO-2010023913 | 3/2010 |
| WO | WO-2016186955 A1 | 11/2016 |

OTHER PUBLICATIONS

Canadian Office Action for Application No. 3076021, dated Jan. 25, 2023, 4 pages.
Chinese Office Action for Application No. 201880069531.2, dated Apr. 28, 2022, 18 pages including translation.
Chinese Office Action for Application No. 201880069531.2, dated Nov. 21, 2022, 6 pages including translation.
Chinese Office Action for Application No. 201880069531.2, dated Sep. 14, 2021, 23 pages including machine translation.
International Search Report and Written Opinion for Application No. PCT/US2018/057399, dated Feb. 28, 2019, 12 pages.

* cited by examiner

LEVER FOR AUTO INSERTION AND SECURE PLACEMENT OF IV TUBING FOR USE IN INTRAVENOUS PUMP SYSTEMS

CROSS-REFERENCE TO RELATED APPLICATION

This is a continuation of U.S. patent application Ser. No. 16/832,363, filed on Mar. 27, 2020, which issued as U.S. Pat. No. 11,892,108 on Feb. 6, 2024, entitled "LEVER FOR AUTO INSERTION AND SECURE PLACEMENT OF IV TUBING FOR USE IN INTRAVENOUS PUMP SYSTEMS," which is a continuation of U.S. patent application Ser. No. 15/793,513, filed on Oct. 25, 2017, which issued as U.S. Pat. No. 10,639,417 on May 5, 2020, entitled "LEVER FOR AUTO INSERTION AND SECURE PLACEMENT OF IV TUBING FOR USE IN INTRAVENOUS PUMP SYSTEMS," the disclosure of which are hereby incorporated by references in their entireties for all purposes.

BACKGROUND

The present disclosure is generally related to intravascular pumps for medication delivery to a patient. More specifically, the present disclosure relates to devices and methods to properly align an infusion tubing in the chassis of an infusion pump to avoid false alarms created by misalignment between the infusion tubing and a sensor configured to monitor the fluid delivery.

SUMMARY

In many intravascular (IV) infusion applications the Directions For Use (DFU) direct the user of an IV medication system to hand-thread the infusion tubing into a slot in the pump casing where a sensor will be able to provide direct measurements of the fluid in the infusion tubing. However, the hand-threading instruction is typically missed by many users, leading to causing excessive false sensor alarms, leading to high inefficiencies in trial and error attempts to properly place the infusion tubing in the sensor slot.

In some aspects of the disclosure, an infusion pump is provided that includes a housing, a door assembly coupled to the housing, a sensor disposed within the housing and a lever disposed within the housing. The lever includes a first end comprising a wall configured to engage an infusion tubing, a second end comprising a pocket, a spring disposed in the pocket, the spring configured to bias the lever against the door assembly and a pusher disposed on the first end, the pusher configured to align the infusion tubing with the sensor when the door assembly is closed.

In some aspects of the disclosure, a method of operating the infusion pump is provided. The method includes loading an infusion tubing into the housing, closing the door assembly to cause the first end of the lever to pivot, pushing the infusion tubing adjacent the sensor and activating the infusion pump when the sensor indicates that the infusion tubing is properly aligned with the sensor.

BRIEF DESCRIPTION OF THE DRAWINGS

In the figures, elements having the same or a similar reference numeral have the same or similar functionality or configuration, unless described as otherwise.

DETAILED DESCRIPTION

For infusion pump applications, the proper placing of an infusion tubing within the pump casing is a critical step. When the infusion tubing is not placed properly, the AIL sensor may tend to sound an alarm for improper positioning. Accordingly, in typical prior art systems the AIL sensor may generate multiple false alarms when the infusion tubing is not properly placed within the sensitive elements in the AIL sensor. Accordingly, health care personnel may have to repeatedly accommodate the infusion tubing to guarantee a proper medication infusion procedure. This causes inefficiencies and may create serious health care outcomes when a medical emergency demands quick and reliable operation.

Embodiments as disclosed herein largely mitigate the above problem by automating the precise location of the infusion tubing in a slot of the AIL sensor to properly read an air-in-line state and avoid a false alarm activation. A false alarm may be caused by an improper installation of the IV set, because a user forgets to hand-thread the IV line in the AIL slot so that the alarm goes off as soon as the user closes the door/latch due to improper placement of the infusion tubing within the AIL housing. False alarms may occur after infusion starts, when the infusion tubing is near the edge of the AIL sensor range, e.g., too far inside, or not far enough within the slot in the AIL sensor. Accordingly, the infusion tubing may be displaced out of the sensing area after infusion starts due to mechanical adjustment, thus trigger a false alarm. Embodiments as disclosed herein provide a solution to the false alarm problem by including a lever that pushes the tubing into position automatically, as a door assembly in the pump casing is closed over the infusion tubing. In addition, embodiments of the present disclosure include features for applying a constant strain relief to the infusion tubing, which have the added benefit of facilitating the positioning of the pump, and the handling of the infusion tubing without the risk of inducing kinks or tears in the tubing.

Some of the advantages of embodiments consistent with the present disclosure include a secure and reliable mechanism for placing infusion tubing in place for IV medication delivery, and simplifying the handling of infusion setups including infusion tubing and pumps in the vicinity of a patient.

Figure 1:
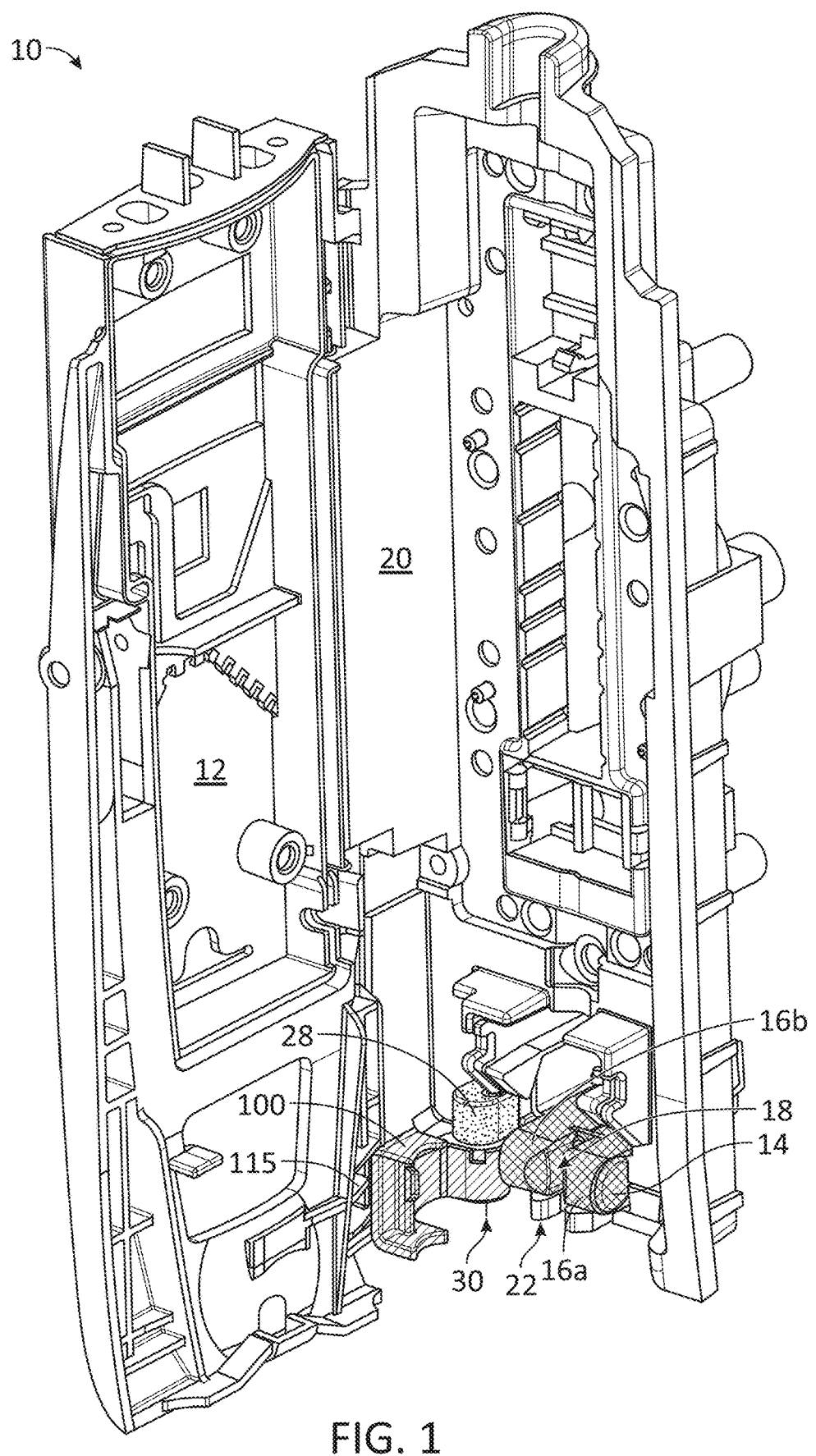
FIG. 1 illustrates an IV casing including a door assembly and an air-in-line (AIL) sensor, according to some embodiments.

FIG. 1 illustrates a pump casing 10 including a chassis 20 and a door assembly 12 hinging over chassis 20 to hold an infusion tubing when closed. Pump casing 10 also includes a lever 100, and an air-in-line (AIL) sensor 14. In some embodiments, AIL sensor 14 may be mounted at a bottom end of chassis 20. AIL sensor 14 may include two sensing elements 16a and 16b (hereinafter, collectively referred to as "sensing elements 16") disposed on two sides of a slot 18. In some embodiments, pump casing 10 includes a bezel 28 mounted on chassis 20 and configured to support a shaft 30. A lever 100 hinges on shaft 30, which allows lever 100 to rotate about the axis of shaft 30. In some embodiments, door assembly 12 includes a reinforced rib 115 on an interior wall of door assembly 12 to engage lever 100 as door assembly 12 rotates to close over chassis 20.

The pump casing 10 further includes a seat 22 shaped to hold infusion tubing 25 and to place the infusion tubing 25 in a gap (e.g., slot 18) formed by the two sensing elements 16 of the air-in-line sensor 14, and wherein the seat 22 comprises a bottom stop 516 (FIG. 5) to stop the infusion tubing 25 in the air-in-line sensor gap when the door assembly 12 is closed.

Figure 2:
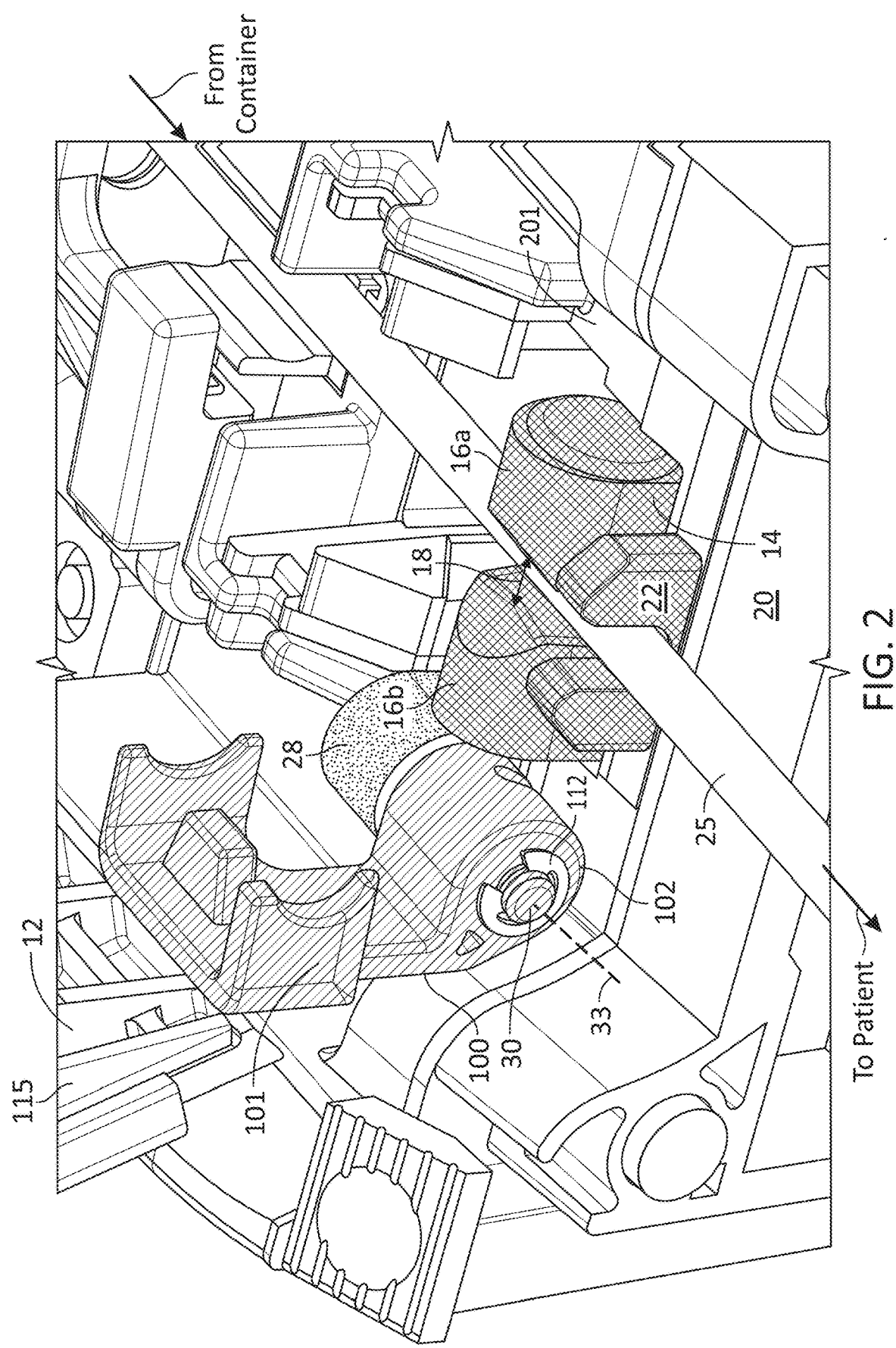
FIG. 2 illustrates a lever driven by the door assembly and configured to place an infusion tubing in the AIL sensor housing at an appropriate depth, according to some embodiments.

FIG. 2 illustrates lever 100, driven by door assembly 12 and configured to place an infusion tubing 25 within AIL sensor 16 at an appropriate depth on a seat 22, according to some embodiments.

Lever 100 includes a far end 101 configured to engage an infusion tubing, and a pivot end 102 configured to fit onto shaft 30 and to allow lever 100 to rotate about a shaft axis 33. In some embodiments, lever 100, further includes a clip 112 to secure lever 100 over shaft 30.

AIL sensor 16 includes a signal (e.g., an ultrasound signal) traveling across the tubing that includes the infusion fluid). Accordingly, infusion tubing 25 should be seated appropriately so that the ultrasound signal in AIL sensor 14 overlaps slot 18 and traverses the fluid.

In some embodiments, chassis 20 further includes a switch 201 to activate the pump mechanism when lever 100 reaches a fully closed position upon closing door assembly 12.

Figure 3:
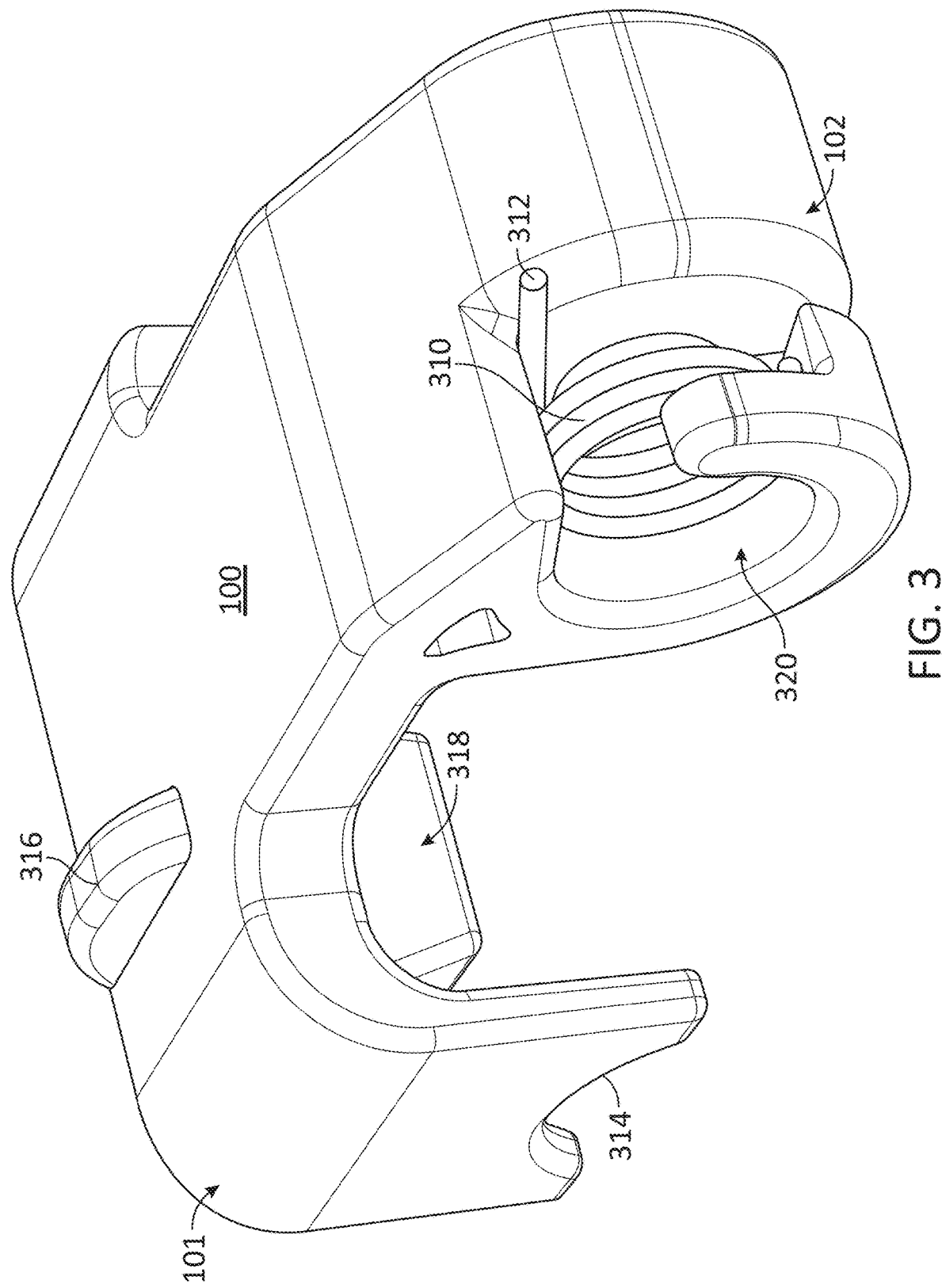
FIG. 3 is a close-up perspective view of the lever in FIG. 2, including a captured spring for automatic unloading when the door assembly is opened, according to some embodiments.

FIG. 3 is a close-up perspective view of lever 100, including a captured spring 310 for automatic unloading when door assembly 12 is opened, according to some embodiments. Pivot end 102 includes a pocket 320 to capture a spring 310 having a leg 312 protruding outside of pocket 320. Spring 310 is configured to bias lever 100 against door assembly 12. In some embodiments, lever 100 includes a tab 316 disposed on an outer side of far end 101 and configured to interface with reinforced rib 115 in door assembly 12. Also, in some embodiments, lever 100 includes a pusher 318 protruding into an inner side of far end 101 and configured to contact infusion tubing 25 when far end 101 engages infusion tubing 25. In some embodiments, pusher 318 is configured to apply a downward pressure to infusion tubing 25 when door assembly 12 is closed. In some embodiments, pusher 318 applies pressure until infusion tubing 25 is properly aligned with sensing elements 16 (cf. AIL sensor 14) disposed on both sides of infusion tubing 25, in slot 18. In some embodiments, pusher 318 comprises a width that fits between the two sensing elements of the air-in-line sensor.

In some embodiments, far end 101 includes two walls 314 (only one visible in FIG. 3) projecting downward to engage the infusion tubing, each of walls 314 being taller than pusher 181 (e.g., reaching further down in FIG. 3) to form infusion tubing 25 longitudinally into an arch. In some embodiments, walls 314 include a trough to accommodate infusion tubing 25. Accordingly, walls 314 push infusion tubing 25 to overlap slot 18 between sensing elements 16 of AIL sensor 14 when door assembly 12 is closed. In some embodiments, when door assembly 12 is closed, walls 314 in lever 100 enshroud seat 22 and sensing elements 16. Accordingly, far end 101 of lever 100 may also act as a mechanical cover and protection to AIL sensor 14, in some embodiments. In embodiments, spring 310 is configured to bias lever 100 against door assembly 12 when door assembly 12 is open and when door assembly 12 is closed.

In some embodiments, lever 100 may be a plastic, injection molded part designed with specific geometry to auto insert infusion tubing 25 through slot 18 in AIL sensor 14. In some embodiments, lever 100 is spring-loaded with geometric features, e.g., tab 316 in far end 101 that mate up with door assembly 12 (e.g., reinforced rib 115) such that when door assembly 12 is closed, it forces the rotation of lever 100 into a closed position, capturing and guiding (e.g., through walls 314) infusion tubing 25 into correct position and depth within slot 18. When door assembly 12 is opened, lever 100, automatically opens by the action of spring 310, thus allowing the user to safely and easily remove infusion tubing 25.

In some embodiments, actuation of lever 100 through spring 310 leverages the closure of door assembly 12, thereby providing forces that push infusion tubing 25 in place (e.g., fully inside slot 18).

Figure 4:
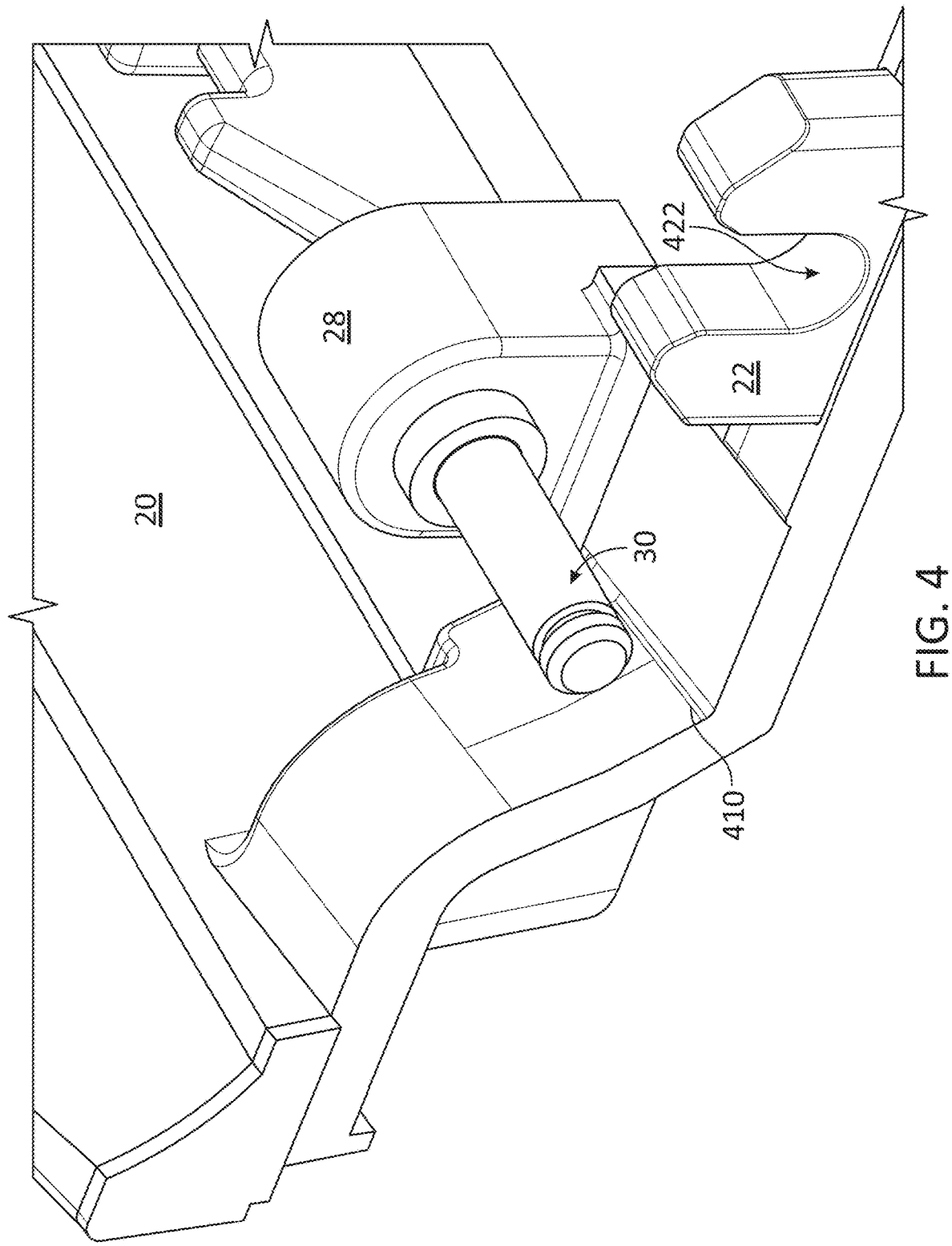
FIG. 4 illustrates a pin configured as a bezel for the lever, according to some embodiments.

FIG. 4 illustrates shaft 30 attached to bezel 28, and configured to support lever 100, according to some embodiments. In some embodiments chassis 20 further includes a groove 410 configured to receive spring leg 312.

Figure 5:
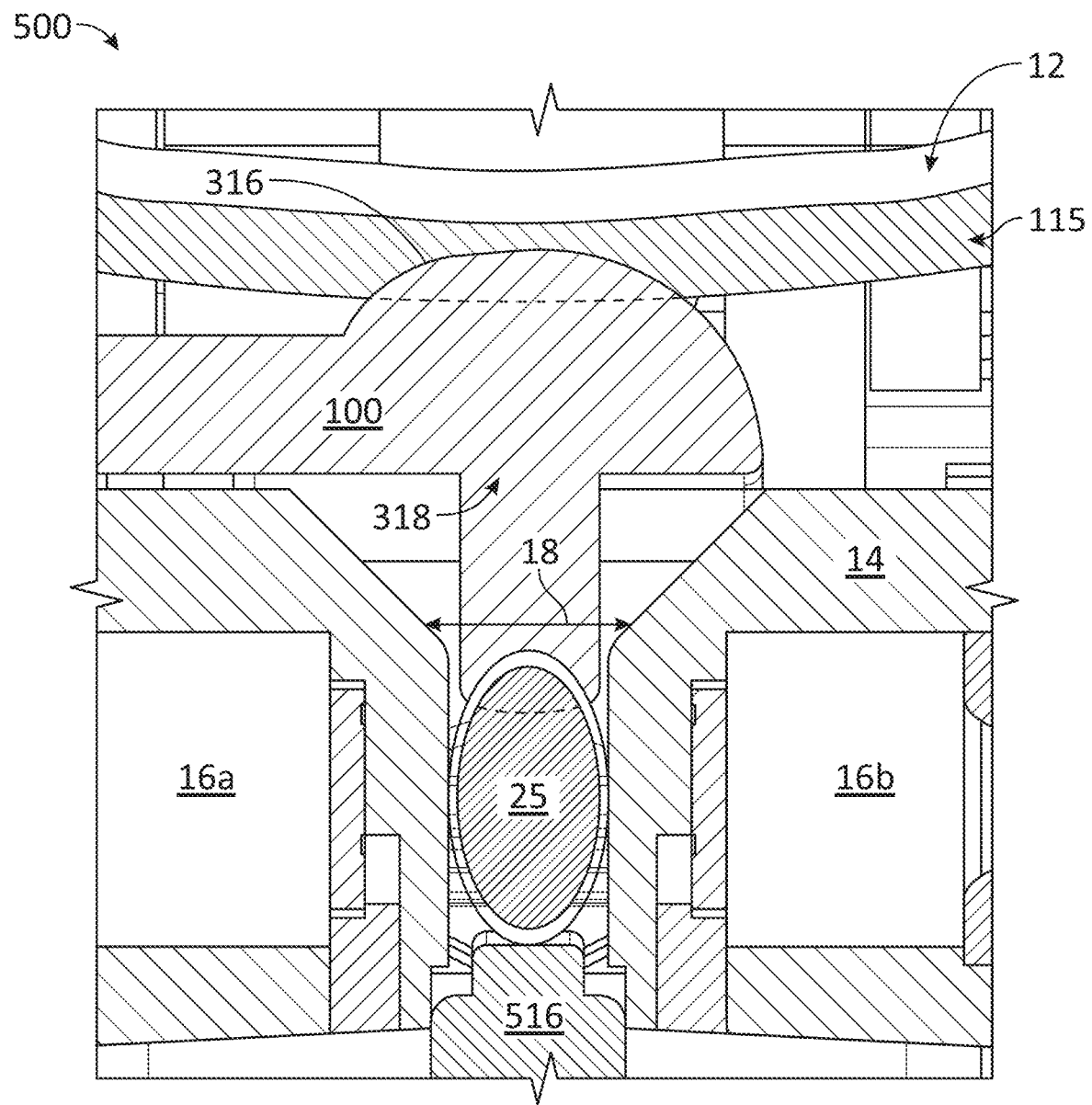
FIG. 5 illustrates a lever to tubing interface when the door assembly is closed, according to some embodiments.

FIG. 5 illustrates a front view 500 of lever 100 interacting with tubing 25 when door assembly 12 is closed, according to some embodiments. In some embodiments, pusher 318 has a height so as to push infusion tubing 25 so far as to overlap with slot 18 forming a sensitive area between sensing elements 16 of AIL sensor 14.

Figure 6:
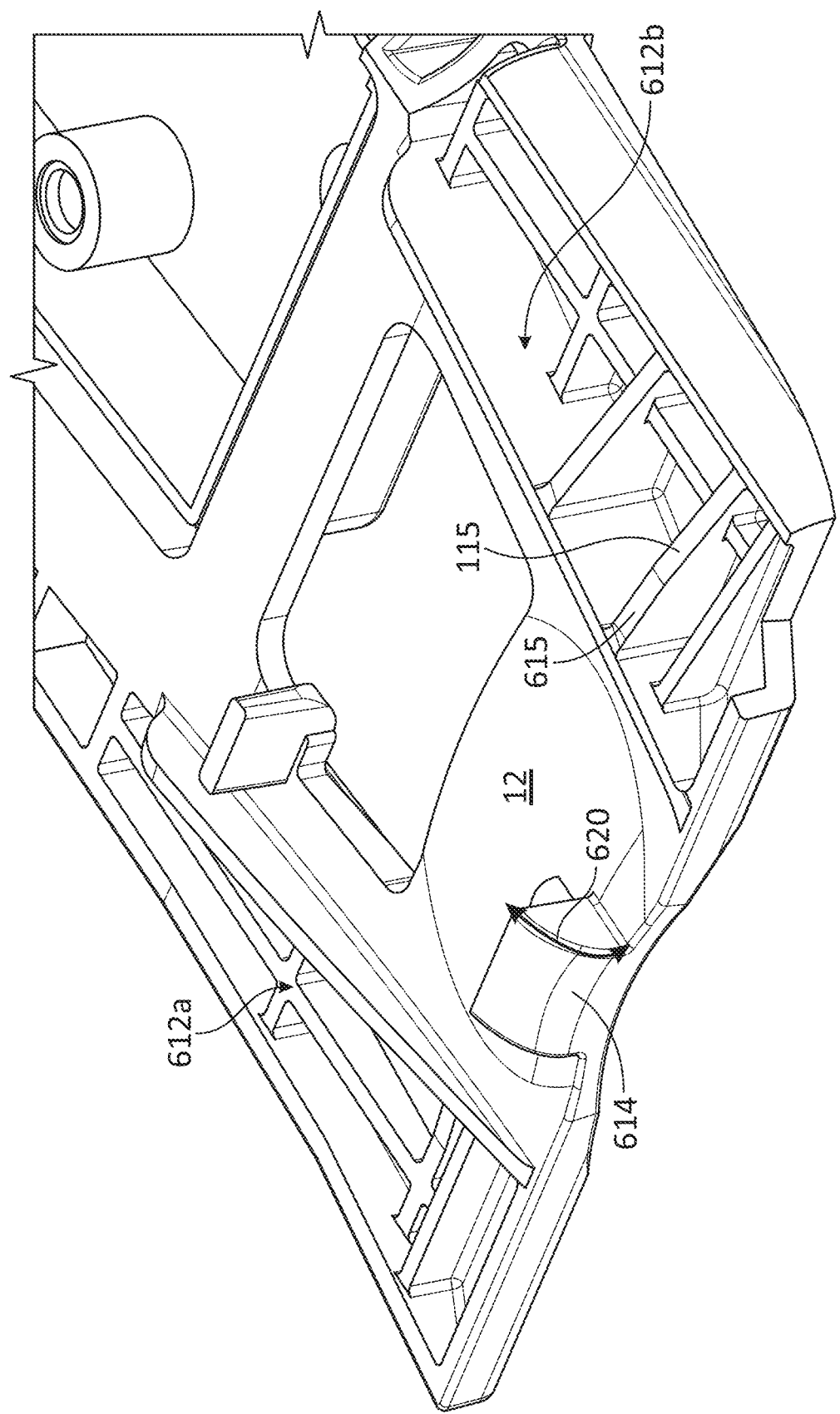
FIG. 6 illustrates a close-up perspective view of a door assembly including reinforced ribs and guiding ribs, according to some embodiments.

FIG. 6 illustrates a close-up perspective view of door assembly 12, including reinforced ribs 612a and 612b, and guiding rib 115 having a flattened edge 615, according to some embodiments. In some embodiments, door assembly 12 includes a protruding feature 614 having an arched surface 620, and configured to relieve stress from infusion tubing 25 (not shown) when door assembly 12 is closed.

Figure 7:
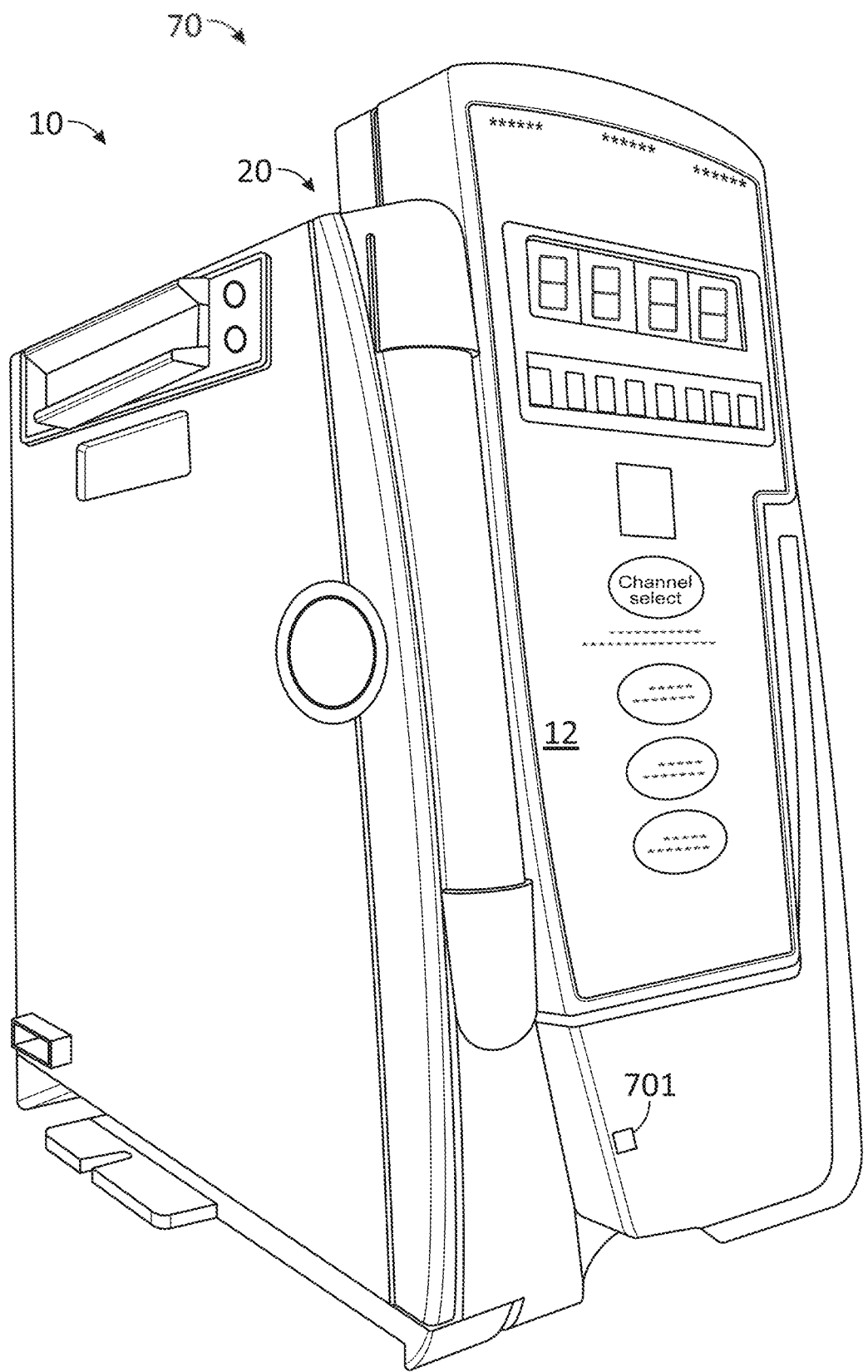
FIG. 7 illustrates an intra-venous pump, according to some embodiments.

FIG. 7 illustrates an intra-venous pump 70 including pump casing 10, door assembly 12, and chassis 20, according to some embodiments. In some embodiments, pump casing 10 may further include an alarm 701 that is activated when infusion tubing 25 fails to fully overlap slot 18 when door assembly 12 is closed.

Figure 8:
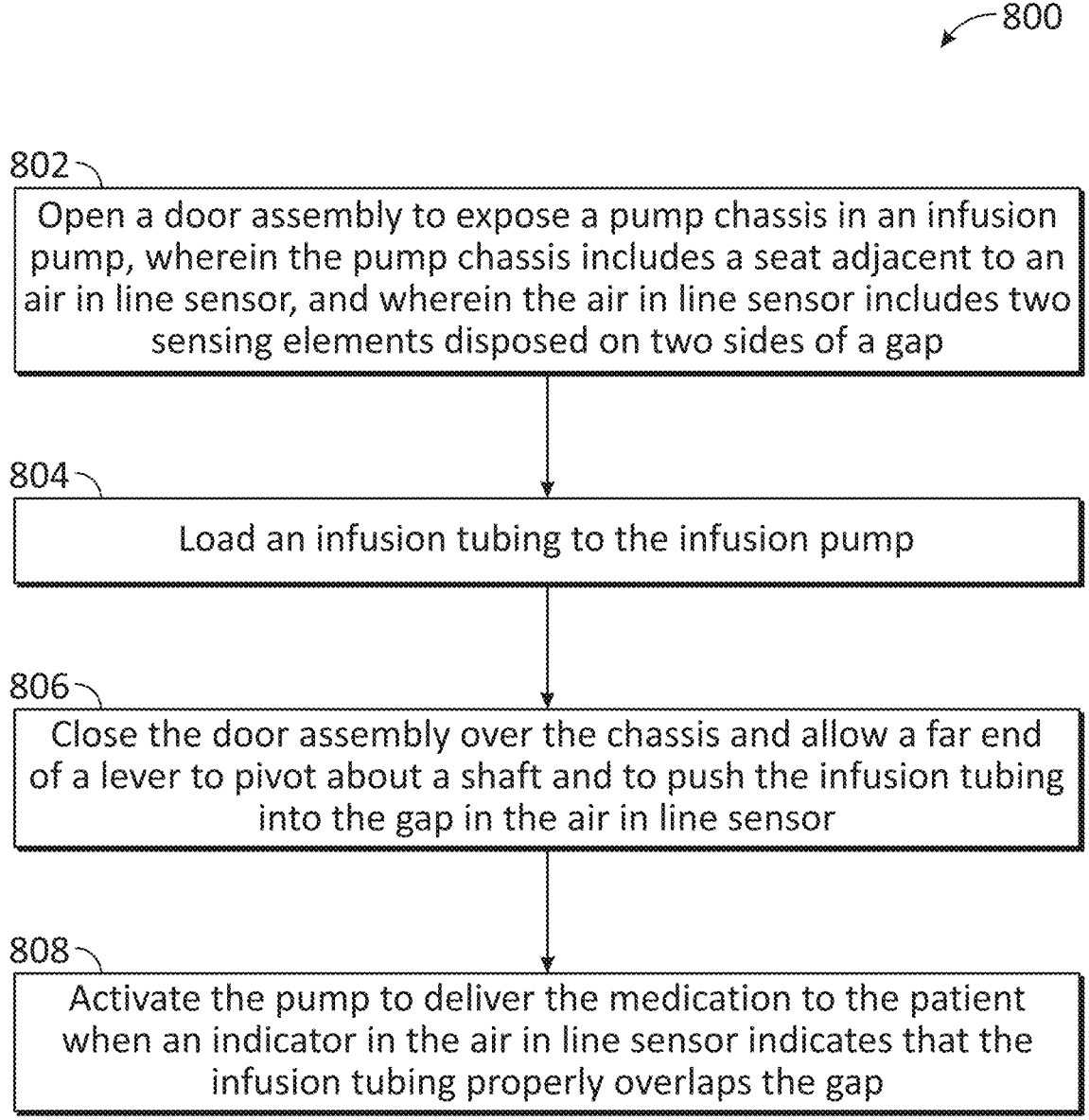
FIG. 8 is a flow chart illustrating steps in a method for delivering a medication to a patient, according to some embodiments.

FIG. 8 is a flow chart illustrating steps in a method 800 for delivering a medication to a patient, according to some embodiments. Step 802 includes opening a door assembly to expose a pump chassis in an infusion pump, wherein the pump chassis includes a seat adjacent to an air-in-line sensor, and wherein the air-in-line sensor includes two sensing elements disposed on two sides of a gap. Step 804 includes loading an infusion tubing to the infusion pump.

Step 806 includes closing the door assembly over the chassis and allowing a far end of a lever to pivot about a shaft and to push the infusion tubing into the gap in the air-in-line sensor. In some embodiments, allowing the far end of the lever to pivot about a shaft in step 806 includes moving the door assembly against the chassis until the indicator in the air line sensor indicates that the infusion tubing properly overlaps the gap. In some embodiments, to push the infusion tubing into the gap in the air line sensor in step 806 includes contacting the infusion tubing with two walls and a pusher in the far end of the lever as the door assembly is closed over the chassis. Further, in some embodiments, to push the infusion tubing into the gap in the air line sensor in step 806 includes contacting a tab disposed on an outer side of the far end of the lever with a reinforced rib on an inner side of the door assembly.

Step 808 includes activating the pump to deliver the medication to the patient when an indicator in the air-in-line sensor indicates that the infusion tubing properly overlaps the gap. In some embodiments, step 808 includes relieving a stress of the infusion tubing with a protruding feature having an arched surface on an inner side of the door assembly.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (e.g., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. An infusion pump, comprising:
 a housing;
 a door assembly coupled to the housing;
 a sensor disposed within the housing; and
 a lever disposed within the housing, the lever comprising:
  a first end comprising a wall configured to engage an infusion tubing;
  a second end comprising a pocket;
  a spring disposed in the pocket, the spring configured to bias the lever against the door assembly and to automatically open the lever when the door assembly is opened; and
  a pusher disposed on the first end, the pusher configured to align the infusion tubing with the sensor when the door assembly is closed.

2. The infusion pump of claim 1, further comprising a tab disposed on an outer side of the first end of the lever, the tab configured to interface with the door assembly.

3. The infusion pump of claim 2, wherein the tab is configured to interface with a reinforced rib on an interior wall of the door assembly.

4. The infusion pump of claim 1, wherein the wall is longer than the pusher, the wall configured to form the infusion tubing into an arc.

5. The infusion pump of claim 1, wherein the wall comprises a trough to accommodate the infusion tubing.

6. The infusion pump of claim 1, wherein the wall is configured to push the infusion tubing to overlap a slot of sensor.

7. The infusion pump of claim 1, wherein the pusher has a height configured to push the infusion tubing to overlap a sensitive area of the sensor.

8. The infusion pump of claim 1, wherein the pusher comprises a width that fits between sensing elements of the sensor.

9. The infusion pump of claim 1, wherein the second end is configured to fit onto a shaft and to allow the lever to rotate about a shaft axis.

10. The infusion pump of claim 9, further comprising a clip configured to hold the lever in place on the shaft while allowing the lever to rotate freely about the shaft.

11. The infusion pump of claim 1, wherein the lever is configured to push the infusion tubing into a seat shaped to hold the infusion tubing and to place the infusion tubing in a slot of the sensor.

12. The infusion pump of claim 11, wherein the lever is configured to push the infusion tubing against a stop of the seat when the door assembly is closed.

13. The infusion pump of claim 11, wherein the wall of the first end is a first wall, the lever further comprising a second wall, wherein the first and second walls are configured to enshroud the seat and the sensor when the door assembly is closed.

14. The infusion pump of claim 13, wherein the first end is configured to be a mechanical and protective cover for the sensor.

15. The infusion pump of claim 1, wherein the spring is configured to bias the lever against the door assembly when the door assembly is open and when the door assembly is closed.

16. The infusion pump of claim 1, wherein the lever is configured to cause a switch to activate a pumping action when the lever reaches a fully closed position upon closing the door assembly.

17. A method of operating the infusion pump of claim 1, the method comprising:
   loading an infusion tubing into the housing;
   closing the door assembly to cause the first end of the lever to pivot;
   pushing the infusion tubing adjacent the sensor; and
   activating the infusion pump when the sensor indicates that the infusion tubing is properly aligned with the sensor.

18. The method of claim 17, further comprising activating an alarm when the infusion tubing is not properly aligned with the sensor when the door assembly is closed.

19. The method of claim 17, further comprising enshrouding the sensor with the first end of the lever when the door assembly is closed to provide a mechanical and protective cover for the sensor.

20. An infusion pump, comprising:
   a housing;
   a door assembly coupled to the housing;
   a sensor disposed within the housing; and
   a lever disposed within the housing, the lever comprising:
      a first end comprising a wall configured to engage an infusion tubing;
      a second end comprising a pocket;
      a spring disposed in the pocket, the spring configured to bias the lever against the door assembly; and
      a pusher disposed on the first end, the pusher configured to align the infusion tubing with the sensor when the door assembly is closed,
   wherein the wall is one of:
      longer than the pusher, the wall configured to form the infusion tubing into an arc; and
      comprising a trough to accommodate the infusion tubing.

* * * * *